(12) United States Patent
Otsuka et al.

(10) Patent No.: US 8,121,666 B2
(45) Date of Patent: Feb. 21, 2012

(54) IMAGE OBSERVATION APPARATUS

(75) Inventors: Satoshi Otsuka, Mitaka (JP); Takashi Fukaya, Tama (JP); Junichi Nozawa, Sagamihara (JP); Tomonori Ishikawa, Hachioji (JP)

(73) Assignee: Olympus Corporation (JP)

( * ) Notice: Subject to any disclaimer, the term of this patent is extended or adjusted under 35 U.S.C. 154(b) by 1722 days.

(21) Appl. No.: 11/190,615

(22) Filed: Jul. 27, 2005

(65) Prior Publication Data

US 2006/0023324 A1 Feb. 2, 2006

(30) Foreign Application Priority Data

Jul. 30, 2004 (JP) ................................. 2004-224665

(51) Int. Cl.
*A61B 5/05* (2006.01)
*F16M 1/00* (2006.01)
*F16M 13/00* (2006.01)
(52) U.S. Cl. .......................... 600/407; 248/637; 248/415
(58) Field of Classification Search .................. 600/407, 600/424; 248/637, 649, 669, 121, 131, 917, 248/415; 348/794, 825, 836; 74/640
See application file for complete search history.

(56) References Cited

U.S. PATENT DOCUMENTS

| | | | |
|---|---|---|---|
| 2002/0186348 A1* | 12/2002 | Covannon et al. | 351/240 |
| 2003/0042772 A1* | 3/2003 | Park | 297/217.1 |
| 2003/0133191 A1 | 7/2003 | Morita et al. | 359/464 |
| 2003/0137731 A1* | 7/2003 | Takahashi et al. | 359/462 |
| 2003/0151809 A1 | 8/2003 | Takahashi et al. | 359/462 |
| 2003/0214710 A1 | 11/2003 | Takahashi et al. | 359/443 |
| 2003/0218720 A1 | 11/2003 | Morita et al. | 351/222 |
| 2004/0085517 A1 | 5/2004 | Togino et al. | 353/31 |

FOREIGN PATENT DOCUMENTS

JP 62-282307 12/1987

(Continued)

OTHER PUBLICATIONS

Office Action issued by the Japanese Patent Office on Jun. 29, 2010 in connection with corresponding Japanese Patent Application No. 2004-224665.

(Continued)

*Primary Examiner* — Long V. Le
*Assistant Examiner* — Katherine Fernandez
(74) *Attorney, Agent, or Firm* — Ostrolenk Faber LLP

(57) ABSTRACT

An image observation apparatus comprising an image display unit for displaying an observation image and a supporting mechanism for supporting the image display unit movably and adjustably in the directions of three, substantially perpendicular axes. Since the supporting mechanism of this image observation apparatus can move and adjust the image display unit in three orthogonal axial directions, an operator need not select a plurality of articulates for operating them when he/she wants to move the image display unit to a desired axial direction. Further, one of the three axes can be a rotational axis for turnably supporting the image display unit around the operator. According to this configuration, the image display unit can be independently moved and adjusted in three axial directions, while the observation angle of the observer with respect to the display face of the image display unit is kept constant.

2 Claims, 14 Drawing Sheets

FOREIGN PATENT DOCUMENTS

| | | |
|---|---|---|
| JP | 1-73841 | 3/1989 |
| JP | 03-012577 | 1/1991 |
| JP | 3-12577 | 1/1991 |
| JP | 4-77971 | 3/1992 |
| JP | 06-043681 | 2/1994 |
| JP | 6-43681 | 2/1994 |
| JP | 07-016238 | 1/1995 |
| JP | 08-066354 | 3/1996 |
| JP | 09-120741 | 5/1997 |
| JP | 11-318936 | 11/1999 |
| JP | 2000-194271 | 7/2000 |
| JP | 2002-008103 | 1/2002 |
| JP | 2003-70854 | 3/2003 |
| JP | 2003-233031 | 8/2003 |
| JP | 2003-233143 | 8/2003 |
| JP | 2003-317455 | 11/2003 |
| JP | 2007-317392 | 12/2007 |
| JP | 2008-168138 | 7/2008 |

OTHER PUBLICATIONS

Translation of Office Action issued by the Japanese Patent Office on Jun. 29, 2010 in connection with corresponding Japanese Patent Application No. 2004-224665.

Japanese Office Action mailed Feb. 8, 2011M connection with corresponding Japanese Patent Application No. 2004-224665 with English Translation.

International Search Report for International Application No. PCT/JP2010/056335 dated May 11, 2010.

Japanese Office Action mailed Feb. 15, 2011 in connection with corresponding Japanese Patent Application No. 2010-534702 with English Translation.

\* cited by examiner

IMAGE OBSERVATION APPARATUS

CROSS-REFERENCE TO RELATED APPLICATION

This application is based upon and claims the benefit of priority from prior Japanese Patent Application No. 2004-224665, filed Jul. 30, 2004, the entire contents of which are incorporated herein by reference.

BACKGROUND OF THE INVENTION

1. Field of the Invention

This invention relates to an image observation apparatus used for observing an operative site in an enlarged scale during a surgical operation. The fields of surgical operations include neurosurgery, ophthalmology and orthopedic surgery and the like.

2. Description of the Related Art

In recent years, surgical operations are often performed in a style in which an image of an operative site is displayed on an image display unit such as an LCD monitor of a display apparatus. The surgeon observes the displayed image on the display unit to carry out a desired treatment. In practice, however, many treating devices or other observation devices are concentrated near the operative site. Therefore, it is desirable that the image observation apparatus be easily installed at a position that does not interfere with those many other devices. Specifically, if the image observation apparatus is located such that the surgeon has to look up, the surgeon becomes fatigued over time. Therefore, as a first requirement, when the image observation apparatus needs to be moved, it is desirable that the image display unit of the image observation apparatus be kept at a sufficient distance from the surgeon within the same horizontal plane, i.e., at the height of the surgeon's eyes.

On the other hand, the surgeon may often need to observe the operative site directly, without using the image observation apparatus. In the course of an operation, the surgeon may need to alternate between using the monitor observation and direct-viewing of the operative site. Therefore, as a second requirement, it is desirable that the image observation apparatus be easily movable away from the operative site when the apparatus is not in use.

In a lengthy operation, moreover, many surgeons often attend the operation alternately. Therefore, as a third requirement, it is desirable that the position of the image observation apparatus be easily adjustable during the operation to accommodate the height of the current surgeon.

In addition to the first to third requirements described above, the image observation apparatus should be sized to save space in the crowded operating room where many devices are arranged around the patient. Therefore, if a supporting device of the image observation apparatus is large-sized or if an additional space is required for the position change of an image display unit, it difficult to arrange necessary devices in the operating room. This difficulty may leads to a problem of lowering efficiency of the operation.

In view of such a problem, JP-A-7-16238 and JP-A-11-318936 have proposed an image observation apparatus, in which a display device such as a monitor is movably provided in three dimensional space with a multi-articulated arm-structure having a plurality of articulations for supporting the image display device. An operator must select a plurality of appropriate arms and actuate the selected arms to locate the display device at a disable position.

JP-A-2003-233031 has proposed an image observation apparatus wherein a display device, as an image display unit, comprises an image projecting unit and a light reflecting member instead of the monitor. The image projecting unit and light reflecting member are arranged to face each other while keeping their relative positions constant through a support member having a similar multi-articulated arm structure. In this display device of JP-A-2003-233031, moreover, there is also disclosed a technique, in which the second requirement can be met by making the light reflecting unit detachable from the support member.

BRIEF SUMMARY OF THE INVENTION

This invention seeks to provide an image observation apparatus comprising: an image display unit for displaying an observation image; and a supporting mechanism that movably and adjustably supports the image display unit along and about three substantially perpendicular axes.

Thus, the observer can move the image display unit in a desirable axial direction without having to select and control a plurality of articulations.

One of the three axial movements can be realized with a rotational axis for rotationally supporting the image display unit around the observer.

According to this configuration, the image display unit can be independently moved and adjusted in three axial directions, one of which includes movement around a rotational axis that traces a locus around the observer, while the observation angle of the observer with respect to the display face of the image display unit is kept constant. As a result, movement of the image display unit can be controlled conveniently and easily without any complicated control being required as in the prior art for adjusting the position of the image display unit finely. Therefore, observer fatigue is reduced, which improves the operation efficiency.

The three axes of the supporting mechanism may include a rotational axis positioned substantially over the cervical vertebrae of the observer.

According to the configuration described above, the image display unit can be independently moved and adjusted around the axis passing through the cervical vertebrae of the observer through the supporting mechanism, while keeping the observation angle of the observer constant. Thus, unlike the prior art, the moving operation is convenient and easy without the need for complicated control to adjust the position of the image display unit finely.

Moreover, the supporting mechanism can include a first rotational axis, which is not a member of the three axes, for turnably supporting the image display unit. In this case, a second rotational axis, which is a member of the three axes, and a linking mechanism for linking the turning angle of the first rotational axis with the turning angle of the second rotational axis is provided.

According to the above configuration, when the position of the image display unit is independently moved and adjusted in the three axes including the second rotational axis through the supporting mechanism, the first rotational axis is rotated through the linking mechanism between the second and first rotational axes according to the rotation of the second rotational axis, and the observation angle is kept constant with respect to the display face of the image display unit. As a result, the moving operation can be likewise made convenient and easy, reducing surgeon fatigue. Moreover, the image display unit can be moved around the first axis so that a simple structure for removing the image display unit is realized. This configuration improves efficiency.

As described above, this invention provides an image observation apparatus with a simple configuration that improves the efficiency of movements and adjustments thereof, and thus, the overall efficiency of the operations.

BRIEF DESCRIPTION OF THE DRAWINGS

These and other features, aspects and advantages of the apparatus and methods of the present invention will become better understood with regard to the following description, appended claims, and accompanying drawings, where:

DETAILED DESCRIPTION OF THE PREFERRED EMBODIMENTS

Embodiments of the invention will be described below with reference to the accompanying drawings.

Figure 1:
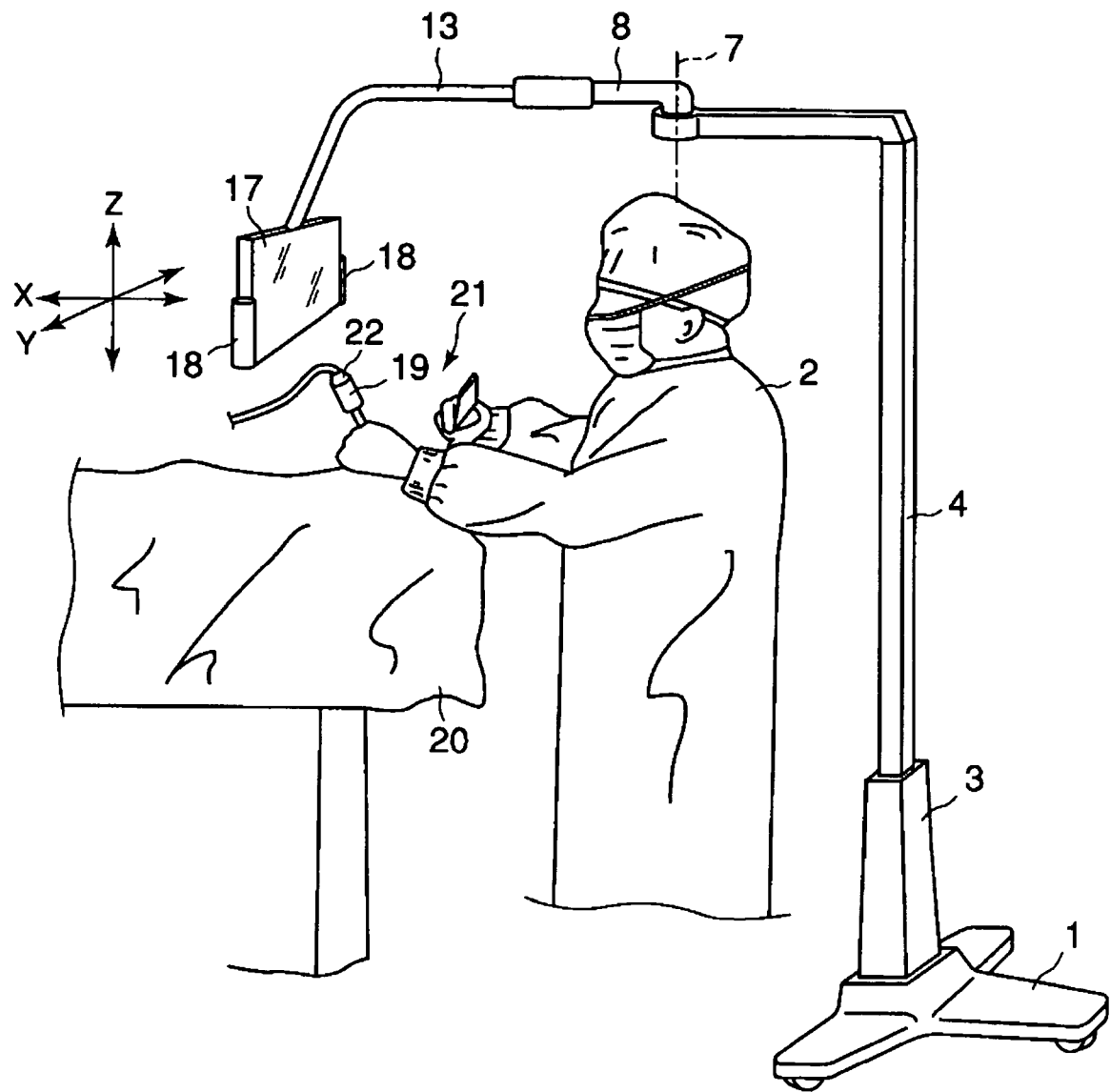
FIG. 1 is a perspective view showing a construction of an image observation apparatus according to a first embodiment of the invention.
Figure 2:
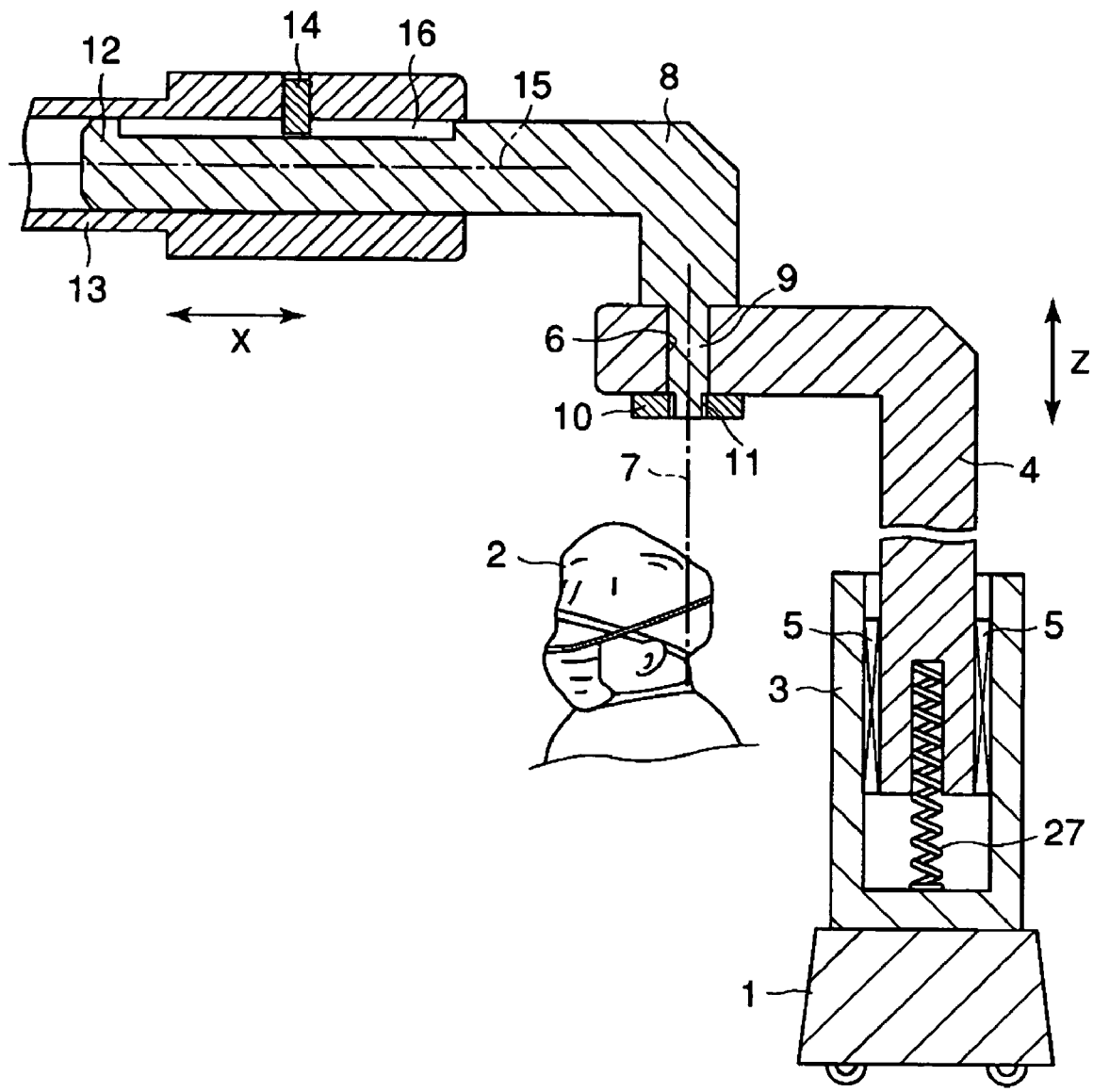
FIG. 2 is a sectional view showing a support structure of FIG. 1.

FIG. 1 shows an image observation apparatus according to a first embodiment of the invention. A base 1 is placed on the floor behind a surgeon 2 or an observer, and a housing 3 of a hollow structure is erected thereon from the base 1. In this housing 3, as shown in FIG. 2, one end of a vertical mover 4 is fitted to move freely in the vertical direction through a cross roller bearing 5. The housing 3, vertical mover 4 and cross roller bearing 5 are contained in a vertical slide mechanism forming part of a supporting mechanism.

Between the lower end of the vertical mover 4 and the housing 3, moreover, there is arranged a balance spring 27, operating under compression. The upper end of the vertical mover 4 is bent toward the surgeon 2 and extends to the vicinity of the head of the surgeon 2. This extension has a through hole 6 formed in its distal end. This through hole 6 has its center axis 7 arranged substantially in alignment with the direction of vertical axis of the cervical vertebrae of the surgeon 2. In this through hole 6, there is inserted turnably and snugly a pivot (rotational axis) 9, which is formed at the proximal end of a turning member 8.

This pivot 9 is equipped at its distal end with a threaded portion 11, which protrudes from the through hole 6 and is fastened by a nut 10. As a result, the turning member 8 is turnably assembled with the through hole 6 of the vertical mover 4. In short, the through hole 6 and pivot 9 are contained in a vertical turning mechanism or journal.

The turning member 8 is formed substantially in an L-shape and has its distal end 12 extended horizontally and toward the surgeon 2 so that the end 12 is inserted slidably and snugly in a longitudinal mover 13 having a substantially hollow structure. In the inner wall near the proximal end of the longitudinal mover 13, a pin 14 protrudes, which snugly fits in a groove 16 formed in the distal end 12 of the turning member 8, in the direction of an extension axis 15 of the distal end 12. The longitudinal mover 13 and the turning member 8 form a longitudinal slide mechanism of the aforementioned supporting mechanism.

To the distal end of the longitudinal mover 13, moreover, is attached an image display unit such as an LCD (Liquid Crystal Display) 17 (FIG. 1). This LCD 17 is equipped at its two sides with operating knobs 18.

Figure 3:
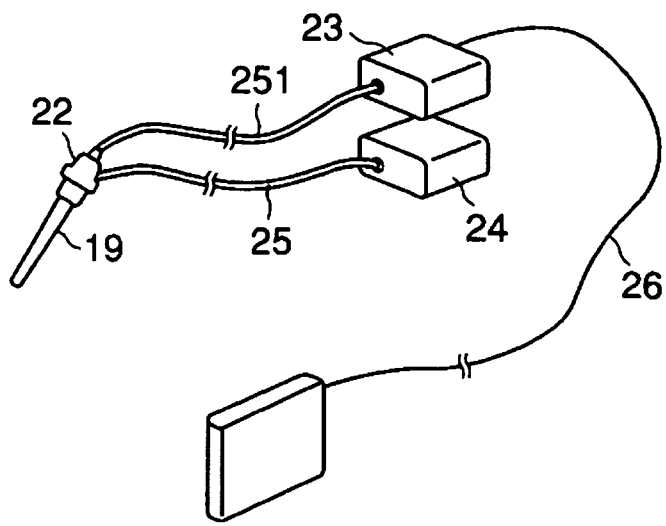
FIG. 3 is a perspective view showing an imaging system of FIG. 1.

In FIG. 1, numeral 19 designates an endoscope, which is gripped by the surgeon 2 and arranged at a desired position of an operative site 21 of a patient 20. This endoscope 19 is optically connected at its proximal end not only to a CCD 22 or the like as an image pickup member but also to a light source device 24 through a light guide cable 25 (FIG. 3). Of these, the CCD 22 is electrically connected through a connection cable 251 with a camera controller 23, which is electrically connected with the LCD 17 through a video signal cable 26.

During surgery with the configuration thus far described, the surgeon 2 inserts at first the endoscope 19 into the operative site 21 of the patient 20 and manipulates the endoscope 19 to take an image of the operative site. The optical image is converted into electric signals by the CCD 22 so that the electric signals are input to the camera controller 23 through the connection cable 251. Then, the camera controller 23 processes the electric signals to create image signals, and outputs the image signals to the LCD 17 through the video signal cable 26 so that the image of the operative site 21 or the observation image picked up by the endoscope 19 is displayed on the LCD 17. Here, the surgeon 2 performs a desired treatment at the operative site 21 while observing the image information displayed on the LCD 17.

Next will be described the works for the surgeon 2 to move the LCD 17 in case the treating device or another observing device interferes with the LCD 17 during the operation. At first, in case the surgeon 2 intends moving the LCD 17 back and forth in the direction of his or her view, the surgeon 2 grips and moves the knobs 18 back and forth in the direction of the arrow X, as shown in FIG. 1. This X-direction control force applied to the knobs 18 is transmitted to the longitudinal mover 13 through the LCD 17. This control force direction is aligned with the direction of the axis 15 of the extension of the distal end 12 of the turning member 8 so that the longitudinal mover 13 slides with respect to the turning member 8. The pin 14 allows sliding movements of the longitudinal mover 13 and the turning member 8 but prevents turning movement therebetween around the extension axis 15. As a result, the LCD 17 slides only in the direction of the extension axis 15 without any turning motion, and its longitudinal position is adjusted.

When the surgeon 2 applies control force to the knobs 18 in the direction of arrow Y, as shown in FIG. 1, the control force is transmitted to the turning member 8 through the LCD 17 and the longitudinal mover 13 so that the pivot 9 is turned relative to the through hole 6. As a result, the LCD 17 is turned around the center axis 7. This center axis 7 is substantially aligned with the cervical vertebrae of the surgeon 2. Without changing the body position with respect to the operative site, therefore, the surgeon 2 is enabled to face the LCD 17 at all times by turning his or her head toward the LCD 17. This control force in the direction Y is perpendicular to the axial direction of the extension axis 15 so that the aforementioned longitudinal mover 13 does not move relative to the turning member 8.

Next will be described the case, in which the LCD 17 is removed so that the surgeon may observe the operative site in a direct view during a series of operations. At first, the surgeon 2 grips the knobs 18 of the LCD 17 and applies the control force in the direction of Z, as shown in FIG. 1. This control force, as applied to the knobs 18, is transmitted through the longitudinal mover 13 and the turning member 8 to the vertical mover 4. The cross roller bearing 5 arranged between the housing 3 and the vertical mover 4 is permitted to move only in the direction Z so that the LCD 17 is moved in the direction Z.

At this time, the weight of the structure from the LCD 17 to the vertical mover 4 is supported by the action of the balance spring 27. Even if, therefore, the surgeon 2 releases the knobs 18, the LCD 17 does not naturally move in the vertical direction but is held at the moved position. Thus, the surgeon 2 can move, if necessary, the LCD 17 upward away from the operative site 21.

Even if another surgeon 2 having a different body size takes over during the operation, the LCD 17 can be set in the desired state by the same controls. Specifically, the position adjustment of the LCD 17 in the height direction due to the difference in the heights of the surgeons can be easily made by the moving adjustment in the direction Z.

Thus, by the image observation apparatus, the LCD 17 displaying the observing image is made adjustable independently of the three substantially perpendicular axis directions X, Y and Z including the turning axis positioned substantially on the cervical vertebrae of the surgeon 2. The axial direction is the direction to which each axis allows the LCD 17 (display unit) to move.

In the image display device of the first embodiment, a simple configuration is realized without using the arm structure of a complicated link mechanism, such as an electromagnetic brake or the like. Moreover, highly precise movement adjustment of the LCD 17 can be realized to greatly contribute to improvements in the operation efficiency.

The first embodiment has been described for the case in which an observation image such as the image of the operative site is captured by using the endoscope 9. However, the invention is not be limited thereto but can be used to display image information acquired by other well-known devices such as stereoscopic endoscopes, surgical microscopes, ultrasonic diagnostic apparatus, MRIs, CTs and the like. In case image information having a parallax is guided to the eyes of the surgeon 2 as in the stereoscopic endoscope apparatus or the surgical microscope, a display part such as the aforementioned LCD 17 can be replaced by the so-called "parallax barrier" type three-dimensional image display apparatus or the like, as disclosed in JP-A-5-107663. This replacement is likewise applicable to all the other embodiments.

Moreover, the first embodiment has been described for the case where the vertical balance utilizes the balance spring 27. But, this balance spring may also be replaced by a coil spring or a counter weight.

Moreover, the first embodiment has been described for the case in which the cross roller bearing 5 is used in the vertical slide mechanism and in which the slip bearing structure is used in the longitudinal slide mechanism. However, the invention is not be limited thereto, but those mechanisms can be additionally configured by using various regulating members such as spline bearings for moving the two members in only one moving direction relative to each other.

Figure 4:
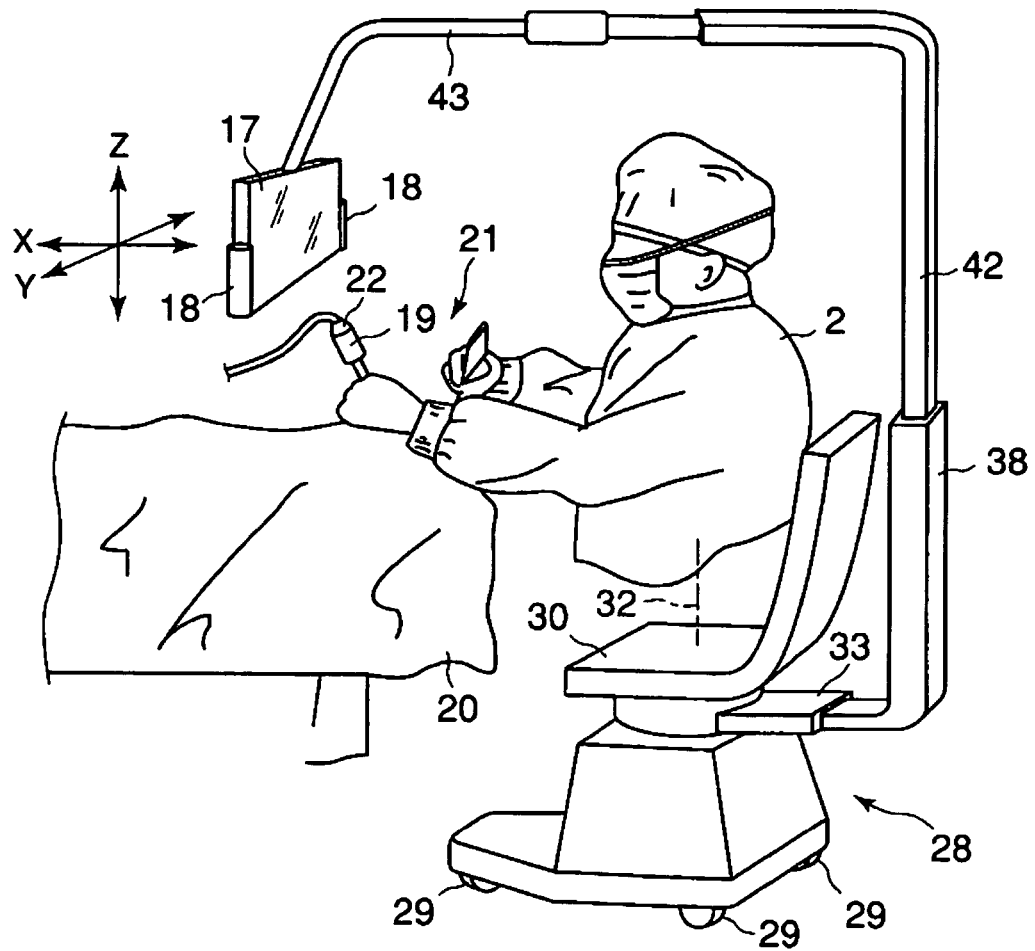
FIG. 4 is a perspective view showing a construction of an image observation apparatus according to a second embodiment of the invention.
Figure 5:
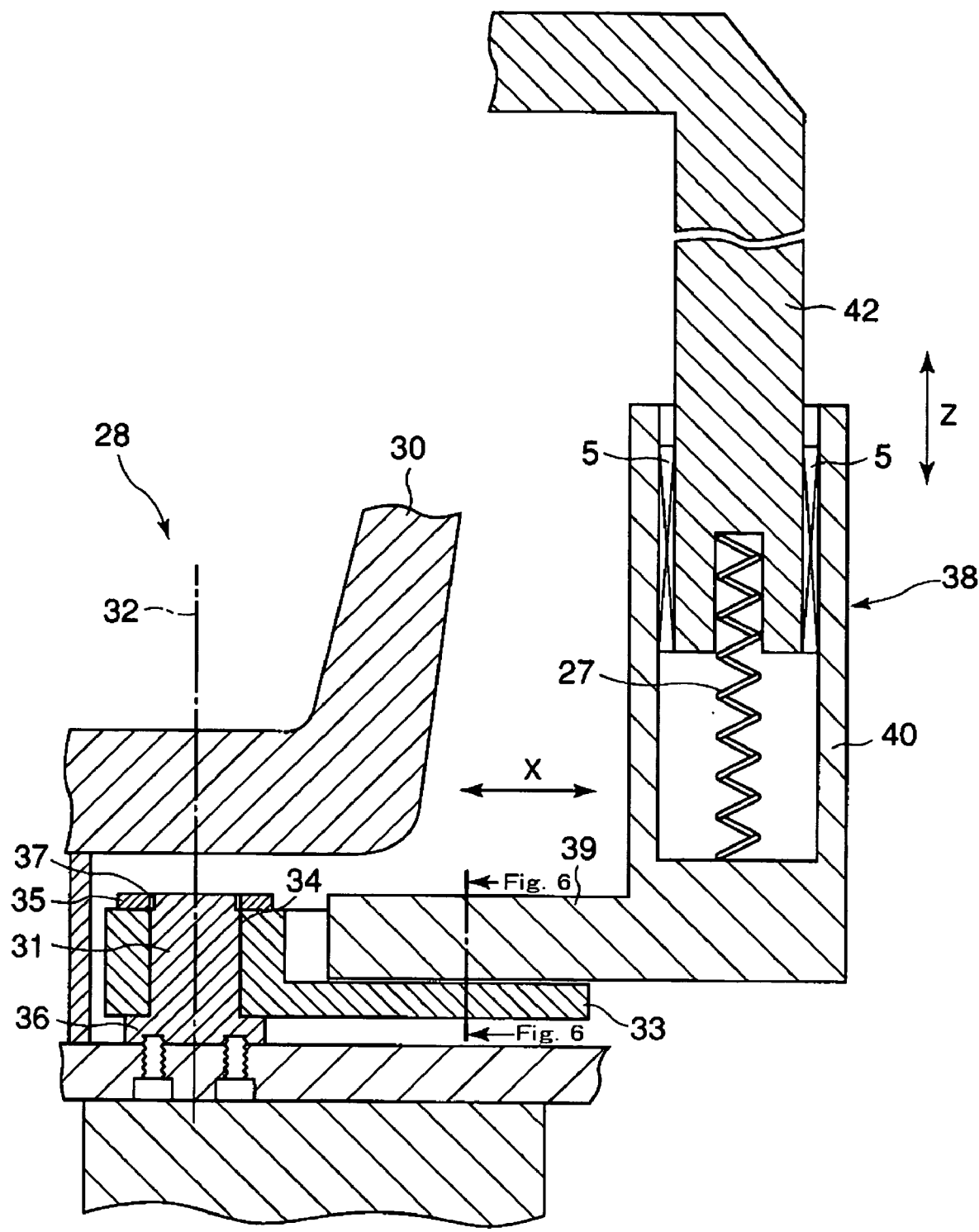
FIG. 5 is a sectional view showing a support structure of FIG. 4.
Figure 6:
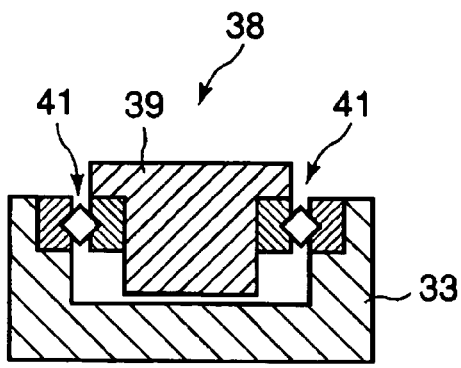
FIG. 6 is a sectional view indicated in FIG. 5.

FIG. 4 to FIG. 6 show an image observation apparatus according to a second embodiment of the invention. In FIG. 4 to FIG. 6, portions identical to those of the first embodiment have the same common reference numerals and perform the same functions.

This embodiment provides a chair 28 for the surgeon 2 to sit on during the operation, which chair is equipped on its bottom with casters 29 at predetermined positions, to enable the surgeon 2 to move on the floor selectively. This chair 28 has a seat 30 (FIG. 5) and a vertical pivot 31 below the seat 30. This vertical pivot 31 has a center axis 32 substantially aligned with the cervical vertebrae of the surgeon 2 when the surgeon 2 is seated. The vertical pivot 31 is inserted in a through hole 34 formed in a support member 33 thereby to support the support member 33 snugly and turnably.

The vertical pivot 31 is provided at its proximal end with a flanged portion 36 corresponding to the through hole 34 and at its distal end with a threaded portion 37. As a result, the vertical pivot 31 is turnably assembled with the support member 33 by inserting its threaded portion 37 from one side into the through hole 34 of the support member 33 and by fastening a nut 35 on its threaded portion 37 while its flanged portion 36 abuts the circumference of one side of the through hole 34. The vertical pivot 31, the support member 33 and the nut 35 are contained in a vertical turning mechanism.

The sectional shape of the support member 33 is substantially a C-shape, preferably having its upper side opened (FIG. 6). The support member 33 is horizontally extended to the back of the surgeon 2, i.e., the seat 30. In the recess of that support member 33, moreover, there is housed one such horizontal portion 39 of a substantially L-shaped vertically moving housing 38 snugly movable in the extending direction through a cross roller bearing 41 composing the longitudinal slide mechanism.

This vertical moving housing 38 has its other vertical portion 40 formed into a hollow structure to receive a vertical mover 42 through the cross roller bearing 5 and the balance spring 27 substantially as in the first embodiment. Moreover, the vertical mover 42 is bent at its upper end toward the surgeon 2 into an L-shape having an upper end, to which the aforementioned LCD 17 is attached through an arm member 43. In the described embodiment, the LCD 17, the surgeon 2 and the extending direction of the support member 33 are arranged to lie substantially on one line.

For the described configuration, the manner of moving the LCD 17 is now described for the case where an operating device or another observing apparatus interferes with the LCD 17 during the operation. In case the LCD 17 is moved back and forth in the viewing direction of the surgeon 2, the surgeon 2 grips the knobs 18 to bring the LCD 17 back and forth in the arrow direction X, as shown in FIG. 4. Then, the control force in the direction X, as applied to the knobs 18, is transmitted to the vertical moving housing 38 through the LCD 17, the arm member 43 and the vertical mover 42. Here, the vertical moving housing 38 is arranged movably in the direction X with respect to the support member 33 through the cross roller bearing 41 so that it is horizontally moved in the direction X with respect to the support member 33 thereby to bring the LCD 17 in the horizontal direction.

When the surgeon 2 applies the control force to the knobs 18 in the direction of arrow Y, as shown in FIG. 4, the control force is sequentially transmitted as in the aforementioned case of the movement in the direction X and finally to the support member 33. Then, the vertical pivot 31 engaging with the through hole 34 of the support member 33 is so turnably arranged as to have its turning direction aligned to the direction Y so that the LCD 17 is turned around the center axis 32 and positionally adjusted in the direction Y.

In this second embodiment, too, as in the first embodiment, the vertical pivot 31 of the chair 28 is aligned substantially with the position of the cervical vertebrae of the surgeon 2. As a result, the surgeon 2 always remains facing the LCD 17 merely by turning his or her neck without changing his or her body position with respect to the operative site.

Now will be described the case in which the LCD 17 is removed for the surgeon 2 to observe the operative site directly, for example during a series of operations. In this case, the surgeon 2 grips at first the knobs 18 of the LCD 17 and applies the control force in the direction of arrow Z, as shown in FIG. 4. Then, the control force applied to the knobs 18 is transmitted to the vertical mover 42 through the LCD 17 and the arm member 43. As a result, the LCD 17 is moved in the direction Z as in the first embodiment, so that it assumes a non-interfering position.

For surgeons of different body sizes who alternate during the operation, the movements and adjustments are made in the directions X, Y and Z in the control procedure as described above. For example, the position adjustment of the LCD 17 in the height direction due to the height difference of a particular surgeon 2 is made by adjusting the movements in the direction Z.

According to the second embodiment, no mechanical portion is provided in the vicinity of the operative site, owing to the arranging of the longitudinal slide mechanism and the vertical turning mechanism below the seat 30 of the surgeon 2. As a result, it is possible to utilize space more effectively.

Moreover, the configuration is made as such those mechanisms are arranged in the assembly of the seat 28 for the surgeon 2. As a result, when the surgeon 2 is seated on the chair 28, the turning center necessarily aligns substantially with the cervical vertebrae of the surgeon 2. Therefore, the surgeon 2 can concentrate on the operating procedures without paying attention to the position of the turning center or his or her position. This contributes to improving the operation efficiency.

Figure 7:
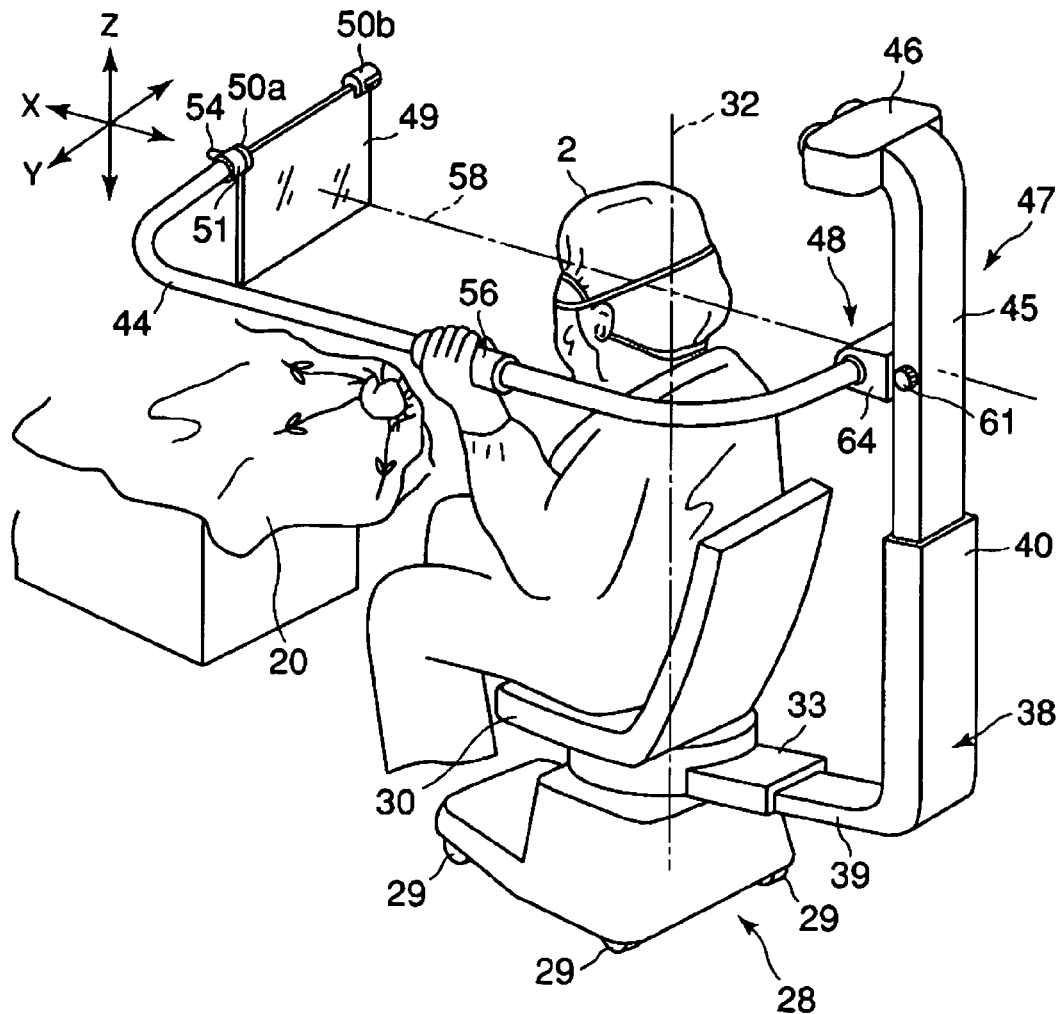
FIG. 7 is a perspective view showing a construction of an image observation apparatus according to a third embodiment of the invention.
Figure 8:
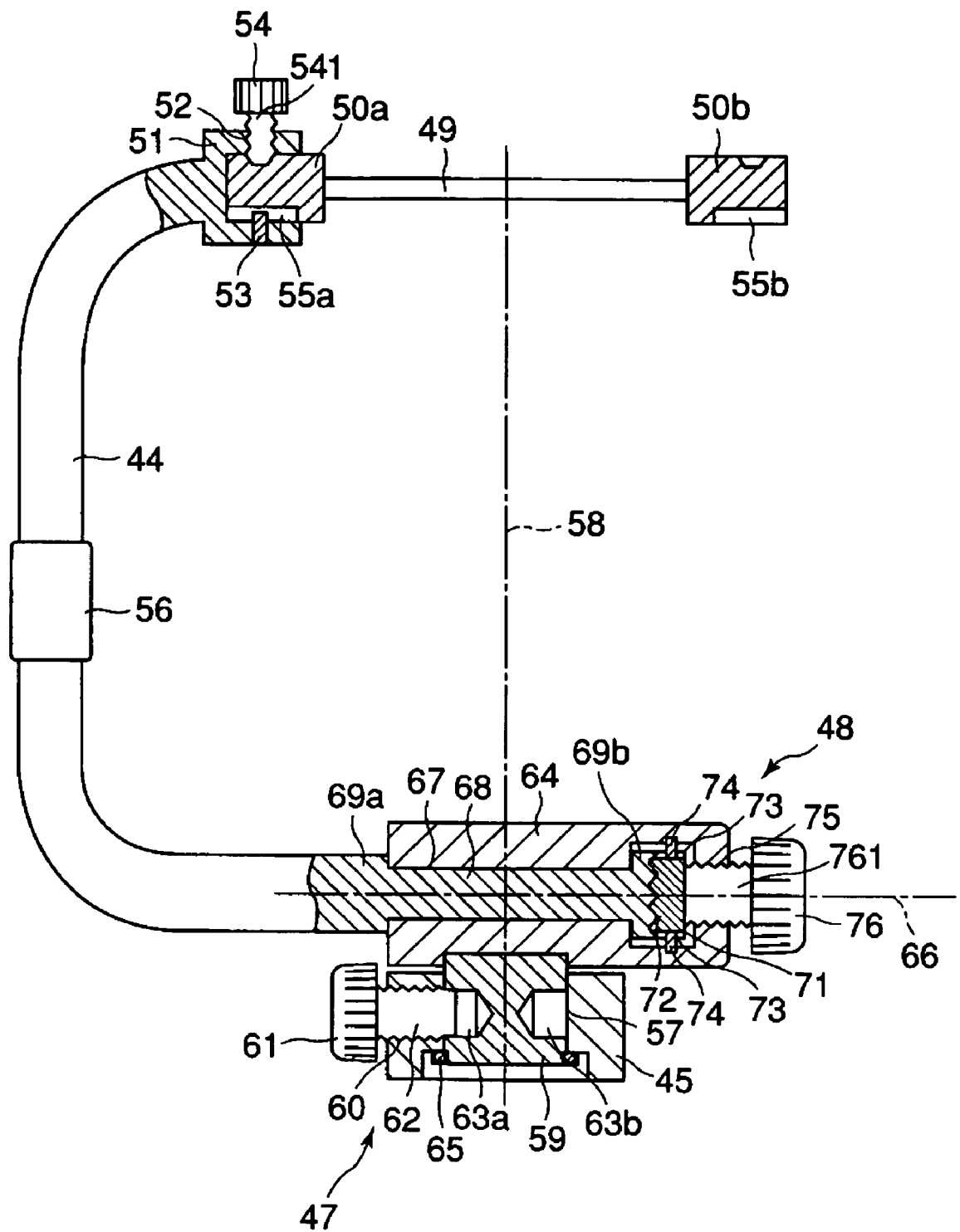
FIG. 8 is a partially sectional view showing a portion of a support structure of FIG. 7.

FIG. 7 and FIG. 8 show an image observation apparatus according to a third embodiment of the invention. In FIG. 7 and FIG. 8, the portions that correspond to those of the first and second embodiments are not described, but bear the same reference numerals.

In the third embodiment, the configuration from the seat 28 to the vertical moving housing 38 is substantially similar to that of the second embodiment. The lower end of a vertical mover 45 is movably inserted (as in the second embodiment) into the vertical portion 40 of the vertical moving housing 38.

To the upper end of the vertical mover 45 are attached a pair of image projecting units 46 or the image projecting mechanism disclosed in JP-A-2003-233031, for example. At an intermediate portion of the vertical mover 45 there is arranged a horizontal arm unit 44 through a later-described transverse switching mechanism 47 and a later-described horizontal arm unit housing mechanism 48. At the distal end of the horizontal arm unit 44 is arranged an image projection panel 49 or the well-known beam reflecting member disclosed in JP-A-2003-233031. Moreover, the horizontal arm unit 44 is equipped at its intermediate portion with a grasping grip 56.

Now there will be described in detail the transverse switching mechanism 47, which is arranged at the vertical mover 45 (FIG. 8). Specifically, the vertical mover 45 is equipped with a through hole 57 around the center axis 58 of the image projection panel 49. A transverse switching stem 59 is engaged snugly and turnably by that through hole 57. This transverse switching stem 59 is fixed at one end in a housing 64 and is fastened and fixed at its other end by a nut 65.

In the outer circumference of the transverse switching stem 59, are formed a pair of fixing holes 63a and 63b, symmetrically with respect to the center axis 58. These fixing holes 64a and 63b are selectively engaged by the externally threaded distal end 62 of a transverse fixing knob 61. This transverse fixing knob 61 is adjustably fastened in a threaded hole 60 formed in the vertical mover 45.

The details of the horizontal arm unit housing mechanism 48 are as follows. In the housing 64, a hole 67 is formed on a center axis 66 perpendicularly to the center axis 58. In this hole 67 is snugly and turnably inserted a housing stem 68, which is formed at the proximal end of the horizontal arm unit 44. The housing stem 68 of the horizontal arm unit 44 is equipped at its two ends with flanges 69a and 69b, which are formed to correspond to the two ends of the hole 67 of the housing 64. These flanges 69a and 69b clamp the two ends of the hole 67 of the housing 64. The flange 69b on the distal end side is serrated at its end face to engage with a serrated or coarse portion 72 formed on a push member 71.

In the outer circumference of the push member 71 are formed a plurality of grooves 73 at a predetermined interval substantially in parallel with the center axis 66. Pins 74 disposed in the housing 64 are so engaged by those grooves 73 as to slide only in the direction of the center axis 66 thereby to make the so-called "spline structure".

Moreover, a housing knob 76 abuts at its distal end against the end face of the push member 71. Specifically, the housing knob 76 is equipped at its distal end with a threaded portion 761, which is adjustably fastened at the end of the housing 64 in a threaded hole 75 formed around the center axis 66.

The details of a joint structure of the horizontal arm unit 44 and the image projection panel 49 are now described. Specifically, the horizontal arm unit 44 is equipped at its distal end with a cylindrical receiving joint member 51. This receiving joint member 51 is equipped in its side face with a threaded hole 52, which is directed toward the cylindrical center direction of the receiving joint member 51. At a position symmetric to that threaded hole 52 with respect to the cylinder center is disposed a positioning pin 53. This positioning pin 53 protrudes in the cylindrical center direction from the wall face of the inner cylinder of the receiving joint member 51. Moreover, a threaded portion 541 of a fixing knob 54 is adjustably fastened into the threaded hole 52 of the receiving joint member 51.

On the other hand, the image projection panel 49 is equipped on the two upper ends with substantially similar joint members 50a and 50b. One of these joint members 50a and 50b is selectively engaged snugly by the receiving joint member 51. These joint members 50a and 50b are equipped in their longitudinal direction with grooved portions 55a and 55b, one of which is selectively engaged snugly by the positioning pin 53.

Next is described the procedure for moving the image projection panel 49 when the treating device or another observing device interferes with the image projection panel 49 during an operation.

When the surgeon 2 intends moving back and forth the image projection panel 49 in the direction of his or her view, the surgeon 2 grasps the grip 56 to apply the control force back and forth in the direction of arrow X, as shown in FIG. 7. The control force in the direction X, as applied to the grip 56, is transmitted sequentially through the horizontal arm unit 44, the horizontal arm unit housing mechanism 48 and the transverse switch mechanism 47 and further to the vertical mover 45. Then, the X-direction force applied to the vertical mover 45 is transmitted, as in the second embodiment, to the vertical moving housing 38.

Because the cross roller bearing 41 moves only in the direction X between the vertical moving housing 38 and the support member 33, the vertical moving housing 38 is horizontally moved in the direction X with respect to the support member 33 so that the image projection panel 49 and the image projecting units 46 are horizontally moved and adjusted together in the direction X.

When the surgeon 2 applies the control force in the direction of arrow Y, as shown in FIG. 4, to the grip 56, the control force is transmitted in the same order as that for the case of moving in the direction X so that it is finally transmitted to the support member 33. Here, the vertical pivot 31 engaged by the through hole 34 of the support member 33 is turnably disposed in the direction Y so that the image projection panel 49 and the image projecting units 46 are turned on the center axis 32 and adjusted in the direction Y.

As with the first and second embodiments, the vertical pivot 31 is substantially aligned with the cervical vertebrae of the surgeon 2 so that the relation between the relative positions of the image projecting units 46, the image projection panel 49 and the eyes of the surgeon 2 is always fixed. As a result, the surgeon 2 is enabled to continue the observation merely by turning his or her head toward the image projection panel 49 without changing his or her body position with respect to the operation site.

The case where use of the image projection panel 49 is dispensed with so that the surgeon 2 may observe the operation site directly in a series of operations is described as follows. First, the surgeon 2 grasps the grip 56 of the horizontal arm unit 44 and applies a control force in direction of arrow Z, as shown in FIG. 6. This control force applied to the grip 56 is transmitted, in an order substantially similar to that of the aforementioned case of the direction X, to the vertical mover 45. Then, the vertical mover 45 is moved in the direction Z, as in the first and second embodiments, so that the image projection panel 49 and the image projecting units 46 are vertically moved together in the direction Z.

Moreover, when surgeons 2 having different body sizes alternate during an operation, adjusting the height difference in the position of the image projection panel 49 due to the height differences between the surgeons 2 is easily accomplished.

In FIG. 7, moreover, the horizontal arm unit 44 is arranged for lefthand operation. However, this configuration can also be modified such that the horizontal arm unit 44 is arranged on the righthand side according to particular needs. In such modification, the surgeon 2 turns at first the transverse fixing knob 61 to loosen its engagement with the threaded hole 60. Then, the transverse fixing knob 61 releases its externally threaded distal end 62 from the fixing hole 63a of the transverse switching stem 59 thereby to release their mutual engagement. In this state, the transverse switching stem 59 is freely turnable with respect to the through hole 57 of the vertical mover 45. Therefore, the surgeon 2 turns the horizontal arm unit 44 by 180 degrees around the center axis 58. Then, the fixing hole 63b of the transverse switching stem 59 is arranged at a position to confront the transverse fixing knob 61. Thus, the surgeon can alone fasten the transverse fixing knob 61 into the threaded hole 60 and insert the same into the fixing hole 63b of the transverse switching stem 59 so that it is fixed with respect to the vertical mover 45.

Next, the surgeon 2 turns back the fixing knob 54 to loosen it. Then, the joint member 50a and the receiving joint member 51 are released from their fixed states. Then, the surgeon 2 pulls out the image projection panel 49 in the groove direction of the grooved portion 55a of the joint member 50a to relieve the image projection panel 49 from the receiving joint member 51. Subsequently, the joint member 50b is inserted into the receiving joint member 51 by engaging the positioning pin 53 with the grooved portion 55b. Here, the positioning pin 53 and the grooved portion 55b engage so that the image projection panel 49 is arranged at the same position as that when the horizontal arm unit 44 is arranged on the lefthand side of the surgeon 2. Then, the fixing knob 54 is fastened again to fix the joint member 50b and the receiving joint member 51.

To store the apparatus, the surgeon 2 first loosens the housing knob 76 to open the push member 71 slidably in the direction of the center axis 66. Then, the push member 71 is released from the abutting force between the serrated portion 72 and the end face of the flange 69b of the housing stem 68 so that the housing stem 68 can turn on the center axis 66. Here, the surgeon 2 turns the horizontal arm unit 44 downward. When the housing knob 76 is fastened again in this state, the fastening force by the threaded portion 75 urges axially the push member 71 in the direction of the center axis 66 so that the serrated portion 72 of the push member 71 and the end face of the flange 69b come into abutting engagement. Thus, the housing stem 68 is positioned and fixed in the turned position. Here, the push member 71 retains a desired fixing force because its serrated portion 72 abuts against and engages with the serrated end face of the flange 69b.

In addition to effects substantially similar to those of the second embodiment, the third embodiment requires less storage by providing the horizontal arm unit housing mechanism 48. Moreover, the horizontal arm unit 44 is arranged on the side of the surgeon 2 so that the position of the grip 56 is closer to the hand of the surgeon 2. Therefore, the movement of the hand can be reduced for the moving control thereby to lighten surgeon fatigue. This also contributes to improving the operation efficiency.

According to the third embodiment, moreover, the provision of the transverse switching mechanism 47 permits the arrangement of the horizontal arm unit 44 on either side of the surgeon 2 in accordance with need. As a result, it is possible to adjust modes according to the operation's needs, to improve the overall operation efficiency.

The third embodiment should not be limited to the mode described above but can also be configured by adding a retracting mechanism 77 such as one shown in FIG. 9 to FIG. 13. In FIG. 9 to FIG. 13, parts used in third embodiment bear the same designations and will not be described again.

Figure 9:
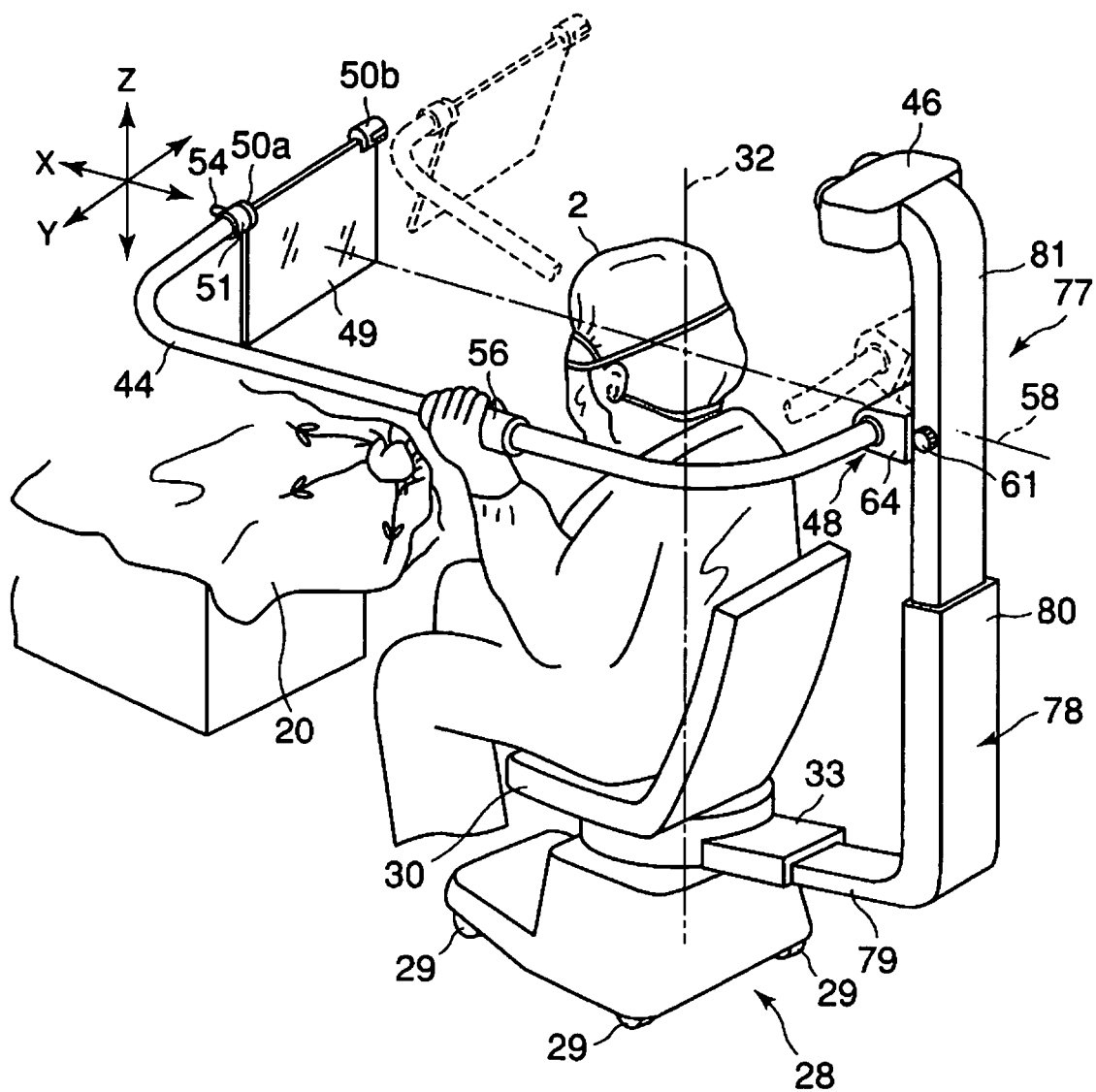
FIG. 9 is a perspective view showing a construction of a modification example of the image observation apparatus according to the third embodiment of the invention.

Specifically, one horizontal portion 79 of a substantially L-shaped vertical moving housing 78 is movably assembled, like the horizontal portion 39 of the vertical moving housing 38, with the chair 28 (FIG. 9). The other vertical portion 80 of the vertical moving housing 78 is formed as a hollow structure, and a vertical mover 81 is jointed to the vertical portion 80 through a vertical slide mechanism 82. The aforementioned image projecting unit 46 or the image projecting mechanism is attached to the upper end of the vertical mover 81.

At the intermediate portion of the vertical mover 81, there are sequentially arranged the retracting mechanism 77 (FIG. 10), a transverse switching mechanism 102 (FIG. 12) and the transverse switching stem 59 which has the same configuration as that of the foregoing third embodiment. This series configuration from the transverse switching stem 59 through the horizontal arm unit 44 to the image projection panel 49 is similar to that of the third embodiment.

Figure 13:
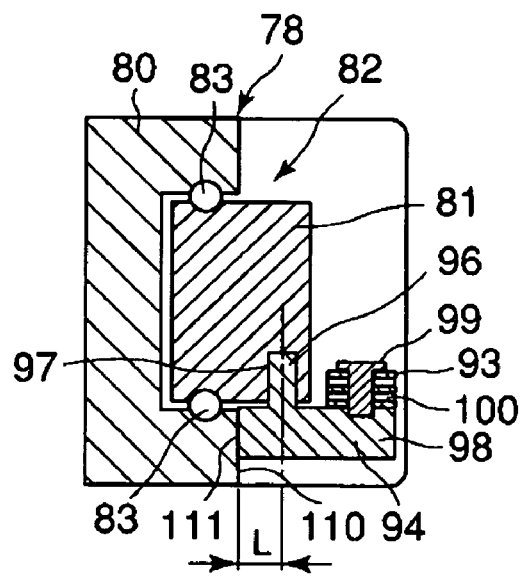
FIG. 13 is a sectional view indicated in FIG. 10.

The details of the vertical slide mechanism 82 are as follows. The vertical mover 81 is inserted movably and snugly only in the direction of arrow Z in FIG. 9 into the inner wall of the vertical portion 80 of the vertical moving housing 78 through a cross roller bearing 83 (FIG. 13). A spring member 84 (FIG. 10) is compressed and arranged between that vertical mover 81 and the vertical moving housing 78.

The spring member 84 is preferably a gas spring for establishing a constant spring force over the entire range in which the vertical mover 81 can move with respect to the vertical moving housing 78. The spring force is substantially equalized to the falling weight, which is exerted from the vertical mover 81 on the spring member 84.

Figure 12:
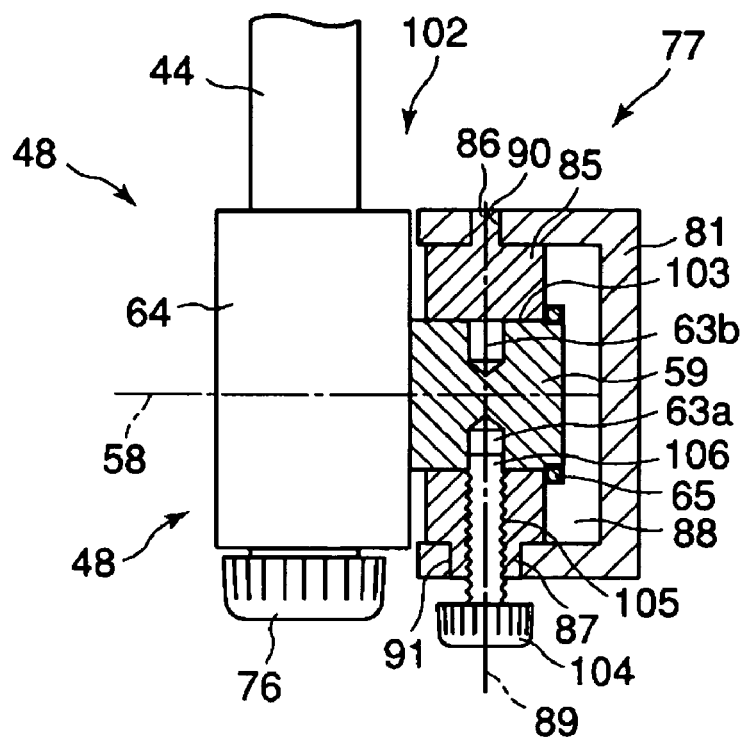
FIG. 12 is a sectional view indicated in FIG. 10.

The retracting mechanism 77 includes a retracting piece 85 constituting the retracting mechanism 77 which comprises on its two side faces two stems of a retracting stem 86 and a hollow retracting stem 87, which are conjugated with respect to the center axis 58 (FIG. 12). On the other hand, the vertical mover 81 is provided with a hollow portion 88 having two side walls, in which through holes 90 and 91 are formed around a retracting stem center 89 perpendicular to the center axis 58. These retracting stem 86 and hollow retracting stem 87 rotatably engage with the through holes 90 and 91, respectively.

Figure 10:
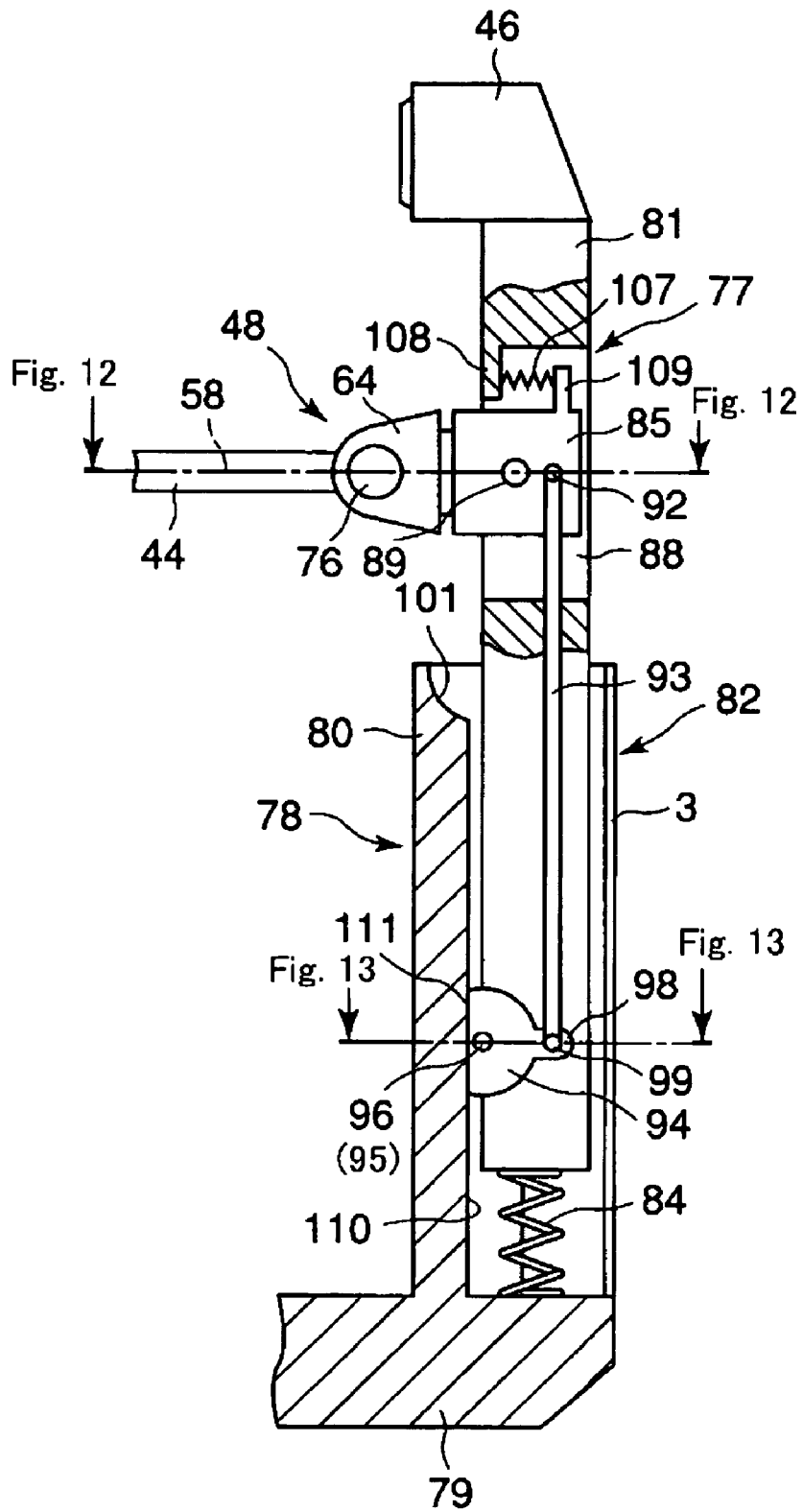
FIG. 10 is a sectional view showing a main part of support structure of FIG. 9.
Figure 11:
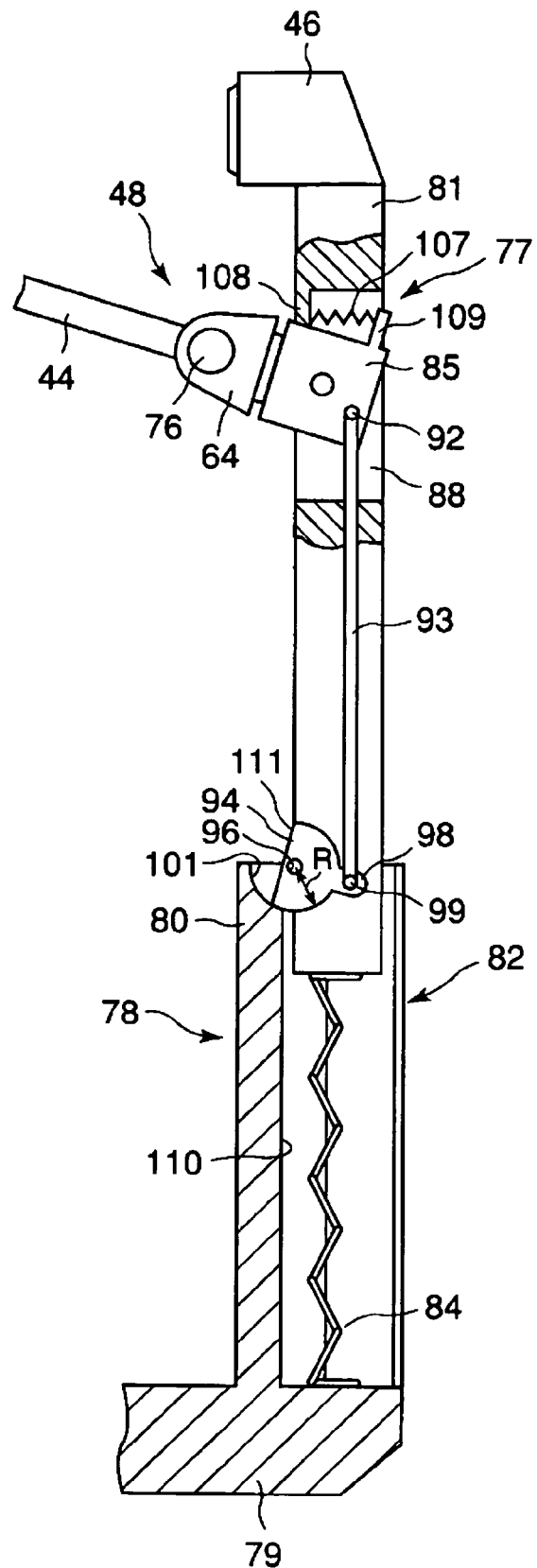
FIG. 11 is a sectional view showing a stowage or protected state of FIG. 10.

From the side of the retracting piece 85, protrudes a pivot pin 92, which turnably supports one end of a link rod 93 (FIG. 11). This link rod 93 is equipped in its other end with a hole 100 (FIG. 13), in which there is turnably inserted a pivot pin 99 of a protrusion 98 embedded in a semicircular plate 94. This semicircular plate 94 is formed substantially into a D-shape by forming a flat portion 111 at a distance L from the center of a disc having a diameter R (FIG. 10 to FIG. 13). From the semicircular plate 94, protrudes a pin 96, which is conjugate with the disc center and which is turnably engaged by a pivot hole 97 formed in the vertical mover 81 (FIG. 13). Moreover, the flat portion 111 of the semicircular plate 94 abuts a flat portion 110 formed on the inner wall of the vertical portion 80 of the vertical moving housing 78 (FIG. 10).

The vertical portion 80 of the vertical moving housing 78 is equipped at its upper end with an R-shaped recess 101, which corresponds to such an R-shape as is conjugate with respect to the center portion of the disc center of the semicircular plate 94. The peripheral wall of the semicircular plate 94 is in sliding contact with that recess 101 (FIG. 11).

Moreover, the retracting piece 85 is equipped at its upper portion with a protrusion 109, which retains one end of a spring 107. The other end of this spring 107 is retained by a protrusion 108, which is formed in the hollow portion 88 of the vertical mover 81.

Next, the transverse switching mechanism 102 will be described in detail. Specifically, the transverse switching stem 59 is engaged snugly and turnably by a through hole 103 formed in the retracting piece 85 (FIG. 12). A threaded portion of a transverse switching knob 104 is adjustably screwed into an internally threaded portion 105 of the hollow retracting stem 87 arranged in the retracting piece 85. The threaded portion of the transverse switching knob 104 is equipped at its distal end with an engagement portion 106, which is snugly retained by the fixing hole 63*a* of the transverse switching stem 59.

The procedure for moving the image projection panel 49 when the treating device or another observing device interferes with the image projection panel 49 during the operation is as follows.

In case the surgeon 2 intends moving the image projection panel 49 back and forth in the direction of his or her view, the surgeon 2 grasps the grip 56 of the horizontal arm unit 44 to apply the control force back and forth in the direction of arrow X, as shown in FIG. 9. The control force in the direction X, as applied to the grip 56, is transmitted through the horizontal arm unit 44, the horizontal arm unit housing mechanism 48, the transverse switch mechanism 47 and the retracting mechanism 77 and further to the vertical mover 81. Then, the control force transmitted to the vertical mover 81 is transmitted as in the third embodiment to the vertical moving housing 78. Then, the vertical moving housing 78 is horizontally moved in the direction X with respect to the support member 33, because it is arranged to move only in the direction X through the cross roller bearing 41 with respect to the support member 33. In accordance with this movement, the image projection panel 49 and the image projecting units 46 are horizontally moved together in the direction X and adjusted.

When the control force is applied by the surgeon 2 in the direction of arrow Y, as shown in FIG. 9, to the grip 56 of the horizontal arm unit 44, the control force is transmitted as in the movement in the direction X to the support member 33. Since the support member 33 is disposed turnably around the vertical pivot 31 engaged by the through hole 34, it has a turning direction aligned to the direction Y. By the turning motions, the image projection panel 49 and the image projecting units 46 are turned together on the center axis 32 and adjusted in the direction Y.

Here, the vertical pivot 31 is substantially aligned with the cervical vertebrae of the surgeon 2 so that the relation between the relative positions of the image projecting units 46, the image projection panel 49 and the eyes of the surgeon 2 is also always maintained. As a result, the surgeon 2 is enabled to continue the observation merely by turning his or her head toward the image projection panel 49 without changing his or her body position with respect to the operative site.

In case the image projection panel 49 is retracted so that the surgeon 2 may observe the operative site in direct view during a series of procedures, the surgeon 2 grasps the grip 56 of the horizontal arm unit 44 and applies a control force in direction of arrow Z (i.e., upward), as shown in FIG. 9. Then, the vertical mover 81 is moved to the uppermost end of the moving range in the direction Z for the vertical moving housing 78, and the retracting piece 85 is turned around the retracting stem center 89 when the control force in the direction Z is further applied. As a result, the image projection panel 49 is turned together with the horizontal arm unit 44 around the retracting stem center 89, as indicated by broken lines in FIG. 9. In these series of controls, during moving in the Z direction, the flat portion 111 arranged in the semicircular plate 94 and the flat portion 110 arranged in the vertical moving housing 78 abut each other so that the semicircular plate 94 does not turn around the disc center 95. As a result, the retracting piece 85 made together with the semicircular plate 94 into a parallel link mechanism does not turn around the retracting stem center 89.

On the other hand, when the vertical mover 81 is positioned at the uppermost end of the moving range in the direction Z, as shown in FIG. 11, the abutment between the flat portion 110 and the flat portion 111 for regulating the turning motions of the semicircular plate 94 around the disc center 95 vanishes so that the retracting piece 85 can turn around the retracting stem center 89. When the surgeon 2 turns the retracting piece 85 around the retracting stem center 89, the semicircular plate 94 forming the parallel link mechanism together with the retracting piece 85 turns around the disc center 95. Then, the R-portion of the semicircular plate 94 comes into abutment against the R-shaped recess 101 arranged in the vertical moving housing 78. In this state, the movement in the direction Z is regulated. By the action of the spring 107, moreover, the balance around the retracting stem center 89 is maintained no matter what the position of the turning state around the retracting stem center 89 of the retracting piece 85. Even if, therefore, the surgeon 2 releases the grip 56, the image projection panel 49 and the horizontal arm unit 44 do not fall, but keep the moving positions.

In case the surgeon 2 changes places during the operation with another surgeon having a different body size, the newly assigned surgeon 2 grasps the grip 56 of the horizontal arm 44 to apply the control force in the direction of arrow Z, as shown in FIG. 9. Then, the control force thus applied to the grip 56 is transmitted as in the case of the direction X to the vertical mover 81 so that the vertical mover 81 is moved in the direction Z by the action of the cross roller bearing 83. In response to the movement of the vertical mover 81 in the direction Z, the image projection panel 49 and the image projecting unit 46 are vertically moved together in the direction Z. Thus, the position adjustment of the image projection panel 49 in the height direction due to the height difference between the surgeons 2 is realized by the movement adjustment in the direction Z.

In addition to the effects of the third embodiment, in the present embodiment, the image projection panel 49 can be brought to and arranged at a higher position than the operative site by the retracting mechanism 77. The image projection panel 49 thus does not interfere with other devices concentrated near the operative site, thereby improving the operation efficiency.

Figure 14:
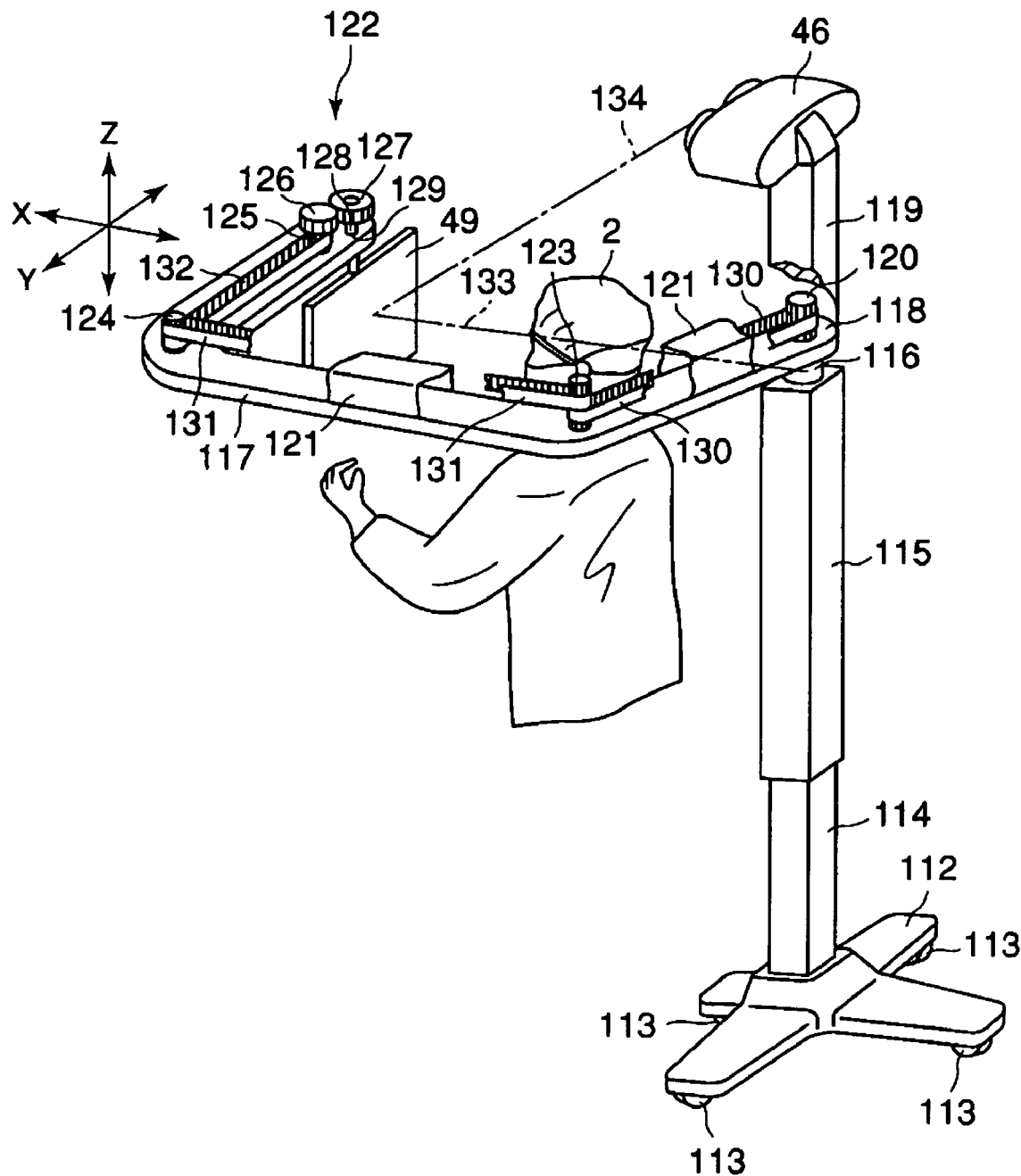
FIG. 14 is a perspective view showing a construction of an image observation apparatus according to a fourth embodiment of the invention.

FIG. 14 shows an image observation apparatus according to a fourth embodiment of the invention. In FIG. 14, portions corresponding to the first to third embodiments are not described, but marked with common reference numerals.

Specifically, a base 112 constituting the supporting mechanism is equipped at its bottom with a plurality of casters 113, which are arranged at a predetermined interval and can move as the longitudinal slide mechanism, for example, only in the direction of arrow X. The image observation apparatus can move on the floor in the direction X with the plural casters 113. From the base 112, there is vertically arranged (in the direction Z) a column 114 having a distal end, onto which a vertical mover 115 acting as the vertical slide mechanism and having a hollow structure is mounted to slide in the vertical direction (the direction Z).

From the upper end of the vertical mover 115, there is arranged a vertical pivot (a rotational axis) 116. This vertical pivot 116 is inserted into a through hole 118, which is formed in one end of a chassis member 117 having a general bow shape so that it is assembled snugly and turnably in the through hole 118. The aforementioned image projecting unit 46 is attached to the chassis member 117 through a column member 119.

On the distal end of the vertical pivot 116, on the other hand, there is turnably fitted a first pulley 120, which constitutes a turn transmission mechanism. On the chassis member 117, moreover, there are individually pivotally mounted a second pulley 123, a third pulley 124 and a fourth pulley 125, which are arranged sequentially at the plurality of curbed portions from the proximal end to distal end of the chassis member 117. These first to fourth pulleys 120, 123, 124 and 125 are preferably set to have equal diameters.

On the upper end of the fourth pulley 125, there is coaxially stacked a drive gear 126 having a pitch circle diameter P. In the distal end of the chassis member 117, moreover, there is formed a through hole 129, in which a stem member 128 is turnably inserted (another rotational axis). On one end of the stem member 128 is fitted a driven gear 127, which meshes with the drive gear 126. To the other end of the stem member 129 is attached the substantially central portion of the upper side of the image projection panel 49. Here, the driven gear 127 has a pitch circle diameter Q and has a module set identical to that of the drive gear 126.

On the other hand, a timing belt 130 runs between the first pulley 120 and the second pulley 123, and a timing belt 131 runs between the second pulley 123 and the third pulley 124. Moreover, a further timing belt 132 extends between the third pulley 124 and the fourth pulley 125. The chassis member 117 is so covered with a cover 121 as to shield the first to fourth pulleys 120, 123, 124 and 125, the drive gear 126 and the driven gear 127. Here, these first to fourth pulleys 120, 123, 124 and 125 are associated through the timing belts 130, 131 and 132 to configure a mechanism for facing an image.

Figure 15:
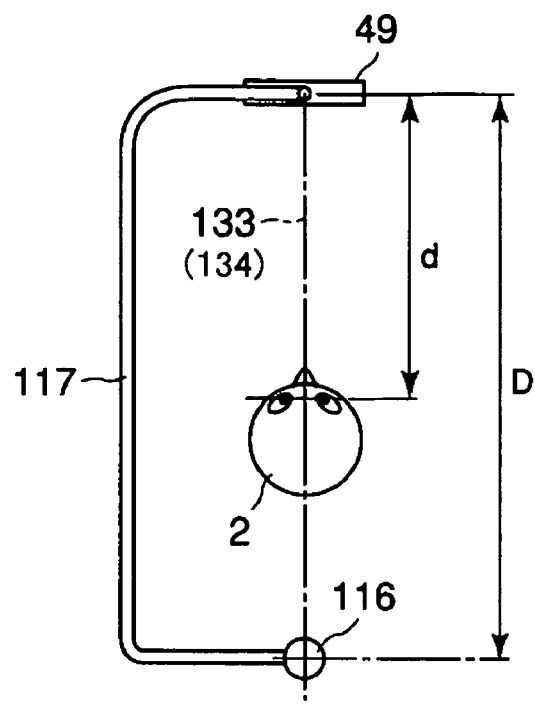
FIG. 15 is a top plan view showing an arrangement and construction of a major portion of FIG. 14.

The image projection panel 49 supported by the stem member 128 of the chassis member 117 is arranged in such relation to the surgeon 2 that the surgeon 2 and the turning center of the vertical pivot 116 are aligned on an axis 133 extending in the normal direction from the center of the image projection panel 49, as shown in FIG. 15. Moreover, the image projected from the image projecting unit 46 in the direction of an axis 134 is so reflected by the image projection panel 49 that it may be focused on the position of a distance d on the axis 133. Here, the surgeon 2, the vertical pivot 116 and the image projection panel 49 are arranged in such a manner that the distance from the image projection panel 49 to the observing position of the surgeon 2 is set to d and the distance from the image projection panel 49 to the center of the vertical pivot 116 is set to D (FIG. 15).

Figure 16:
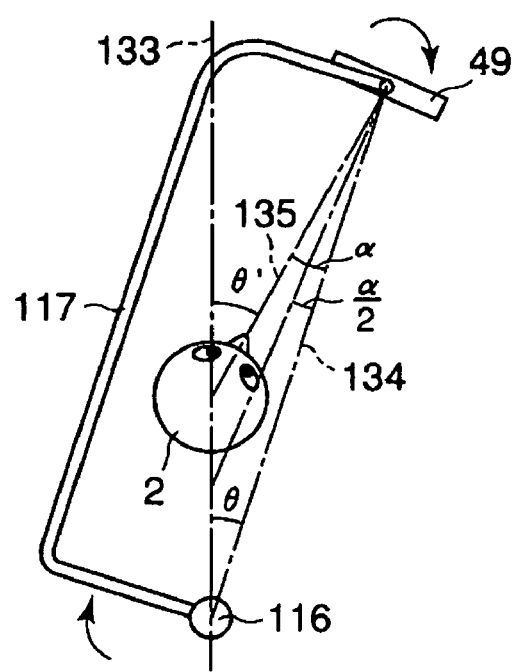
FIG. 16 is a top plan view shown for explaining an adjusting action of FIG. 14.

In case, therefore, the chassis member 117 is turned by θ degrees on the vertical pivot from the position of FIG. 15, an angle of α degrees is made, as shown in FIG. 16, between the axis 134 joining the center of the vertical pivot 116 and the center of the image projection panel 49 and an axis 135 joining the surgeon 2 and the center of the image projection panel 49.

The relation between the reduction ratio ε of the drive gear 126 and the driven gear 127 and the θ is desired to satisfy the following relation, but this relation cannot be realized by the ratio of P/Q of the pitch circle diameters:

$$\epsilon = \{\sin^{-1}(D/d \cdot \sin\theta)\}/2\theta - \frac{1}{2}.$$

For θ=30 degrees, the reduction ration ε1 is expressed by:

$$\epsilon 1 = \sin^{-1}(D/2d)/60 - \frac{1}{2} = P/Q.$$

Here, a series of components from the vertical pivot 116 through the chassis member 117 to the stem member 128 configure a vertical turning mechanism (a linking mechanism).

In the configuration thus far described, the surgeon 2 moves the image projection panel 49 selectively, in case the treating device or another observing device interferes with the image projection panel 49 during the operation. In the first case, in which the surgeon 2 intends moving the image projection panel 49 back and forth in the direction of his or her view, the surgeon 2 grasps the chassis member 117 to apply the control force in the longitudinal direction or the directions of arrow X, as shown in FIG. 14. Then, the control force in the direction X is transmitted through the chassis member 117 and the vertical mover 115 to the column 114. As a result, the casters 113 are forced to move in the direction X so that the apparatus is moved and adjusted in its entirety in the direction X.

When the surgeon 2 applies the control force in the direction Y, on the other hand, the chassis member 117 is turned around the vertical pivot 116. In case the chassis member 117 is turned by θ degrees, as shown in FIG. 16, the first pulley 120 and the chassis member 117 turn relative to each other. Then, the second pulley 123, the third pulley 124 and the fourth pulley 125 are sequentially turned by the timing belts 130, 131 and 132, so that the drive gear 126 is turned by θ degrees. At this time, the drive gear 126 turns the driven gear 127 to turn the image projection panel 49 through the stem member 128. Here, the turning angle of the image projection panel 49, i.e., the turning angle of the driven gear 127, is α/2 degrees according to the relation of the gear ratio of P/Q, as shown in FIG. 16.

Specifically, the driven gear 127 has the following relation to the turning angle α/2, in case the drive gear 126 turns by the angle θ with the drive gear 126 of the pitch circle diameter P and the driven gear 127 of the pitch circle diameter Q meshing with each other:

$$\alpha/2 = P \cdot \theta / Q \quad (1).$$

Next, the following relation holds for the case where the angle between the axis 133 and the axis 135 shown in FIG. 16 is designated by θ':

$$\alpha = \theta' - \theta \quad (2).$$

The following formula is deduced from equations (1) and (2):

$$P/Q = (\theta' - \theta)/(2 \cdot \theta) \quad (3).$$

In the configuration shown in FIG. 16, the following relation holds:

$$d \cdot \sin \theta' = D \cdot \sin \theta \quad (4).$$

The relation of the aforementioned reduction ratio ε can be deduced on the basis of equations (3) and (4).

Now will be described the case in which retraction is taken of the image projection panel 49 so that the surgeon 2 may observe the operative site in direct view during a series of operations, for example. This control is also likewise adjusted in case the surgeons 2 having different body sizes alternate during the operation.

Specifically, the surgeon 2 grasps the chassis member 117 and applies the control force in the direction of arrow Z, as shown in FIG. 14. This control force applied to the chassis member 117 is transmitted, as in the case of the aforementioned control of the direction X, to the vertical mover 115 so that this vertical mover 115 is moved in the direction Z relative to the column 114. As a result, the image projection panel 49 and the image projecting unit 46 are moved together vertically in the direction Z. In other words, the position adjustment of the image projection panel 49 in the height direction due to the height difference between the surgeons 2 is made by the movement in the direction Z.

According to the fourth embodiment, the vertical pivot 116 can be arranged on the axis of the vertical mover 115 having no relation to the position of the cervical vertebrae of the surgeon 2, so that the appearance and shape can be simplified. As a result, it is possible to realize a configuration that is not likely to obstruct the operation, thereby to improve the operation efficiency as much as possible.

The fourth embodiment has been described for the case where the turning angle of α/2 of the image projection panel 49 is determined by the ratio of the pitch circle diameters of the drive gear 126 and the driven gear 127. However, the invention is not limited thereto but can also be configured such that the decision is made by altering the external diameters of the first to fourth pulleys 120, 123, 124 and 125.

Moreover, the fourth embodiment is exemplified by the example using the image projection panel 49 and the image projecting unit 46 disclosed in JP-A-2003-233031, as the image display member. However, the invention is not so limited, but can also be configured by using LCD or other displays. In this modification, however, the turning angle of α/2 should be doubled to α.

Figure 17:
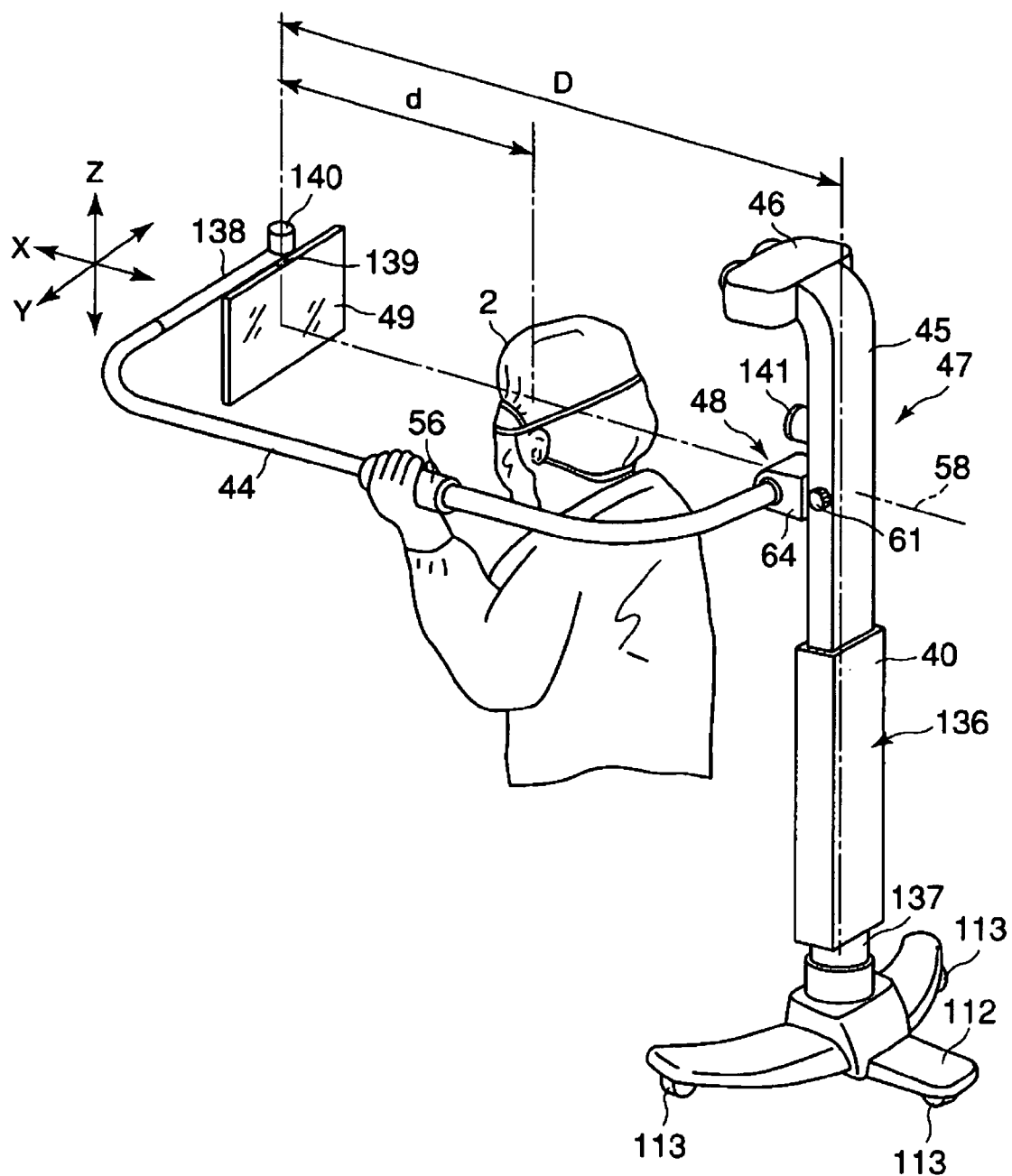
FIG. 17 is a perspective view showing a construction of an image observation apparatus according to a fifth embodiment of the invention.

FIG. 17 shows an image observation apparatus according to a fifth embodiment of the invention. In FIG. 17, portions corresponding to the third embodiment are not described, but merely marked with the same reference numerals.

In this fifth embodiment, the substantially L-shaped vertical moving housing 38 of the third embodiment is replaced by a vertical moving housing 136 having a substantially straight hollow structure. This vertical moving housing 136 is turnably erected at its proximal end from the aforementioned base 112 through a vertical pivot 137. This base 112 is provided with plural casters 113 at a predetermined interval. The image observation apparatus can move on the floor through those casters 113.

Into the distal end of the vertical moving housing 136 is also movably inserted one end of the vertical mover 45, with which the aforementioned horizontal arm unit 44 through the transverse switching mechanism 47 and the horizontal arm unit housing mechanism 48 are associated. To the distal end of the horizontal arm unit 44 is attached an extension arm 138, which extends to the center of the image projection panel 49.

Figure 18:
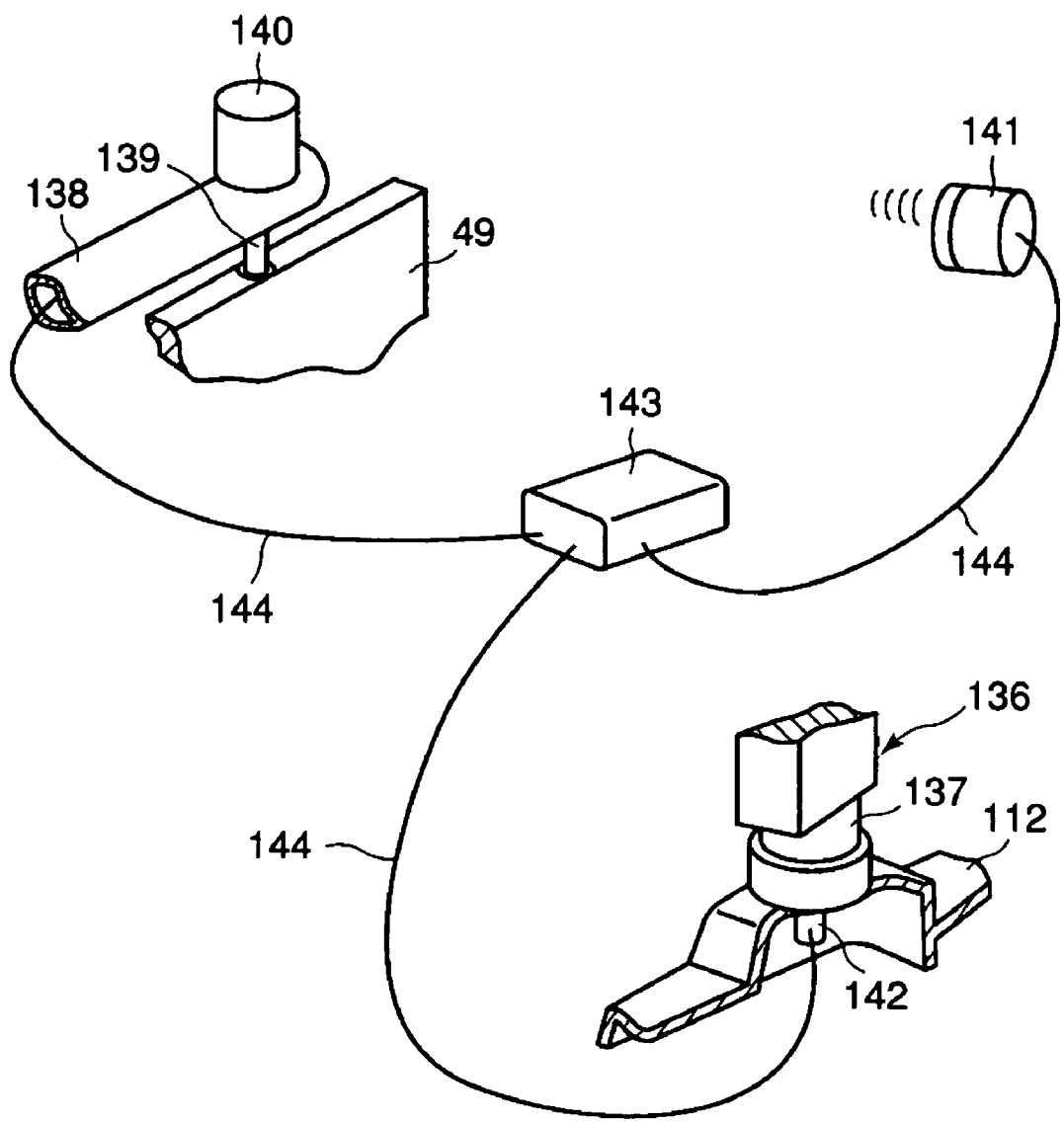
FIG. 18 is a perspective view showing a configuration of a control system of FIG. 17.

At the distal end of the extension arm 138 is provided a panel pivot 139 that can turn in the vertical direction, as shown in FIG. 18. A motor 140 is also arranged at the distal end of the extension arm 138. This motor 140 has its turning output spindle connected to the panel pivot 139. Moreover, the motor 140 is electrically connected through a connection cable 144 with a control circuit 143 contained in the display image confronting mechanism.

At the vertical mover 45, moreover, there is arranged an ultrasonic length measuring device 141, which is positioned on the back of the head of the surgeon 2. At the aforementioned base 112, moreover, there is arranged a rotary encoder 142, which has a turning input shaft connected to the vertical pivot 137. These ultrasonic length measuring device 141 and rotary encoder 142 are electrically connected with the aforementioned control circuit 143 through the connection cable 144.

The control circuit 143 controls the turning angle β of the motor 140 according to the following relation, where the distance from the center of the vertical pivot 137 to the image projection panel 49 is designated by D, the distance from the image projection panel 49 to the observing position of the surgeon 2 is designated by d, and the turning angle of the vertical pivot 137 is designated by θ:

$$\beta = \frac{1}{2} \cdot \{\sin^{-1}(D/d \cdot \sin \theta) - \theta\}.$$

In the configuration thus made, the surgeon 2 grasps the grip 56 and applies the control force in the direction of arrow X, as shown in FIG. 17, in the case where the treating device or another observing device interferes with the image projection panel 49 during the operation. Then, the control force is transmitted to the vertical moving housing 136 through the arm unit 44 and the vertical mover 45 so that the casters 113 of the base 112 raising the vertical moving housing 136 are moved in the direction X to adjust the longitudinal direction.

Where, on the other hand, the surgeon 2 applies the control force in the direction Y to the grip 56, the control force is transmitted to the vertical moving housing 136 through the arm unit 44 and the vertical mover 45 so that the vertical pivot 137 is turned relative to the base 112. This turning angle θ is detected by the rotary encoder 142, which outputs its detection signal to the control circuit 143. Simultaneously with this, the distance from the ultrasonic length measuring device 141 to the surgeon 2 is detected by the ultrasonic length measuring device 141, and the detection signal is input to the control circuit 143. In response, the control circuit 143 calculates the distance d from the image projection panel 49 to the observing position of the surgeon 2, which distance is obtained from the initially given distance D by the ultrasonic distance measuring device 141, and creates a motor drive signal so that the motor 140 is turned by the angle β on the basis of that motor drive signal.

As a result, even where the surgeon 2 moves the image projection panel 49 by turning it by the angle θ around the center of the vertical pivot 137, the surgeon 2 is able to look at the observation image from the image projection panel 49 at all times merely turning only his or her face toward the image projection panel 49, without moving the body.

According to the fifth embodiment, the image projection panel 49 can be reliably directed toward the surgeon 2 by the control of the control circuit 143. Moreover, the controllability can be improved to improve the operation efficiency.

While there has been shown and described what is considered to be preferred embodiments of the invention, it will, of course, be understood that various modifications and changes in form or detail could readily be made without departing from the spirit of the invention. It is, therefore, intended that the invention be not limited to the exact forms described and illustrated, but should be constructed to cover all modifications that may fall within the scope of the appended claims.

What is claimed is:

1. An image observation apparatus comprising:
    an image display section which includes a display surface for displaying an image;
    a supporting unit which includes a body portion provided in a separated state from the image display section in first horizontal directions which are parallel to a normal axis of the display surface, a coupling portion, and a link portion, one end of which is coupled to the body portion and an other end of which is coupled to the image display section, the supporting unit movably supporting the image display section in vertical directions, in the first horizontal directions, and in second horizontal directions which are perpendicular to the vertical directions and to the first horizontal directions, and defining an observing position between the image display section and the body portion;
    a first rotation unit which is configured to rotate the image display section and the link portion with respect to the body portion about a first vertical axis which passes a coupling portion between the body portion and the link portion, and which is configured to move the image display section in the second horizontal directions;
    a second rotation unit is configured to rotate the image display section with respect to the link portion about a second vertical axis which passes a coupling portion between the image display section and the link portion, the second rotation unit including a first gear which rotates together with the image display section about the second vertical axis; and
    an angle adjusting unit which includes a second gear meshing with the first gear, and a transmitting section configured to transmit a driving force that rotates the second gear by rotating the link portion about the first vertical axis, and which is configured to adjust a rotation angle of the image display section about the second vertical axis in a state that a display surface of the image display section faces the observing position, the angle adjusting unit being configured to adjust a reduction ratio ε of the first gear with respect to the second gear in a state of relation of $$\epsilon=\{\sin^{-1}(D/d\cdot\sin\theta)\}/2\theta-\tfrac{1}{2}$$

is satisfied, when an angle between a line joining the first vertical axis and the second vertical axis and a line joining the first vertical axis and the observing position is set to θ, a distance between the image display section and the first vertical axis is set to D, and a distance between the image display section and the observing position is set to d.

2. The image observation apparatus according to claim 1, wherein the link portion includes a column portion which is coupled to the body portion, and an arm portion which is coupled to the column portion in a state that the arm portion is arranged in a first position or in a second position which is symmetrical to the first position about the normal axis of the display surface.

* * * * *